United States Patent [19]

Kakimoto et al.

[11] Patent Number: 5,056,124

[45] Date of Patent: Oct. 8, 1991

[54] METHOD OF AND APPARATUS FOR EXAMINING OBJECTS IN CONTAINERS IN NON-DESTRUCTIVE MANNER

[75] Inventors: Kenichi Kakimoto; Toshitaka Kobayashi, both of Higashimurayama; Masanori Nagata, Tokyo; Shigeki Imano, Tokyo; Hideaki Honma, Tokyo; Hideki Nishiyama, Tokyo, all of Japan

[73] Assignees: Meiji Milk Products Co., Ltd.; Fujimori Kogyo Co., Ltd.; Softex Co., Ltd., all of Tokyo, Japan

[21] Appl. No.: 527,732

[22] Filed: May 23, 1990

[30] Foreign Application Priority Data

May 24, 1989 [JP] Japan .................................. 1-130380

[51] Int. Cl.$^5$ ...................... G01N 23/04; G01N 23/06; G21K 5/08
[52] U.S. Cl. ......................................... 378/57; 378/53; 378/66
[58] Field of Search ..................... 378/51, 53, 54, 57, 378/58, 52, 62, 66

[56] References Cited

U.S. PATENT DOCUMENTS

| | | | |
|---|---|---|---|
| 3,768,645 | 10/1973 | Conway et al. | 378/58 |
| 3,958,078 | 5/1976 | Fowler et al. | 378/57 |
| 4,415,980 | 11/1983 | Buchanan | 378/58 |
| 4,722,096 | 1/1988 | Dietrich et al. | 378/57 |
| 4,769,830 | 9/1988 | Peterson et al. | 378/57 |
| 4,791,655 | 12/1988 | Nagata et al. | 378/57 |
| 4,879,734 | 11/1989 | Schreckendgust et al. | 378/57 |

Primary Examiner—Edward P. Westin
Assistant Examiner—Kim-Kwok Chu
Attorney, Agent, or Firm—Wenderoth, Lind & Ponack

[57] ABSTRACT

Method and apparatus for enabling fluid material contained in a package to be examined in a non-destructive manner to see whether there is any unacceptable alteration in the material. This examination is accomplished by shaking the package so that the package and its contents vibrate at the natural resonance frequency thereof, exposing the package to an irradiation of ultra-soft X-ray beams while the package is vibrating at the resonant frequency, either immediately after the package contents begin to be agitated by shaking or immediately after the vibration is stopped and it ceases to be agitated, detecting the strength of X-rays transmitted through the package and its contents, coverting the transmitted X-rays to a corresponding analog signal, and determining any alteration by comparing the analog signal against the refernece signal previously obtained in the same manner as described above for a like package with unaltered contents.

5 Claims, 2 Drawing Sheets

METHOD OF AND APPARATUS FOR EXAMINING OBJECTS IN CONTAINERS IN NON-DESTRUCTIVE MANNER

BACKGROUND OF THE INVENTION

1. Field of the Invention

The present invention relates to a method of and an apparatus for examining materials, such as liquids, pastes and others having fluidity, that are contained in bottles and like containers to form a package, in order to determine whether there are any abnormal alterations such as defects in those objects without destroying the package. More specifically, the present invention provides means whereby a package containing a material is shaken under a particular vibration condition, the package is then exposed to an irradiation of ultra-soft X-ray beams that are directed against the surface of the package either immediately after it begins to be agitated due to the shaking or immediately after the vibration is stopped and it ceases to be agitated, the strength of the X-ray beams that have been transmitted through the package and its contents is detected by an X-ray beam meter means, and there can be detected any change and/or magnitude of such change in the density per unit volume of any mixture of gas in any space other than that occupied by the content that may exist within the package (which space will hereinafter be referred to as "head space") and the content itself. Through those steps, it can be determined whether the material contains any abnormal property alteration, and if it does, how much the material is affected by such alterations.

2. Description of the Prior Art

During the product quality control process, it is important that the finished products, particularly foods contained in containers to form packages, should be checked to see whether there are any abnormal alterations in the properties. For canned foods, a conventional testing method is provided whereby those contents are examined by striking the can from the outside to determine whether there are any unusual or abnormal material property alterations. For other articles, a conventional non-destructive testing method detects any difference between the normal (unaltered) or abnormal (altered) material conditions visually, or by using an image resolution or analysis technique, from the surface of the liquid that is fluctuating when the package is shaken under vibration. A typical conventional non-destructive testing method and apparatus are disclosed in Japanese patent applications unexamined publication nos. 63-167249 and 63-271146, respectively, whereby a package to be examined which contains a liquid, for example, is shaken to cause an agitated condition, and then the package is exposed to an irradiation of ultra-soft X-ray beams which is directed against it, from which an appropriate video signal information is obtained. This video signal information reflects the state of distribution within the head space, from which any abnormal alterations and/or the magnitude thereof can be determined. The method and apparatus as described above cannot be applied in some cases, and in those cases, an appropriate number of packages must be sampled by opening those samples to allow them to be checked to see whether there are any abnormal material property alterations.

The above conventional non-destructive method, which has primarily been used to examine the contents by striking the container from the outside, can only be applied to canned goods. Similarly, the method, as also described above, which consists of shaking a package to agitate the contents and then determining any abnormal alterations from the way in which the liquid surface is fluctuating, may only be applied to those types of packages through which the contents can be seen. Since most packages are not transparent, this method has limited application.

For the method and apparatus as disclosed in the patent applications cited above, a video signal may be formed from the amount of X-ray beams that have been transmitted through the package. When this video signal is converted into a fluorescent image which may appear on a screen, an afterimage will remain on the screen for a certain length of time. If individual tests occur consecutively, each test must wait until the image from the preceding test has disappeared from the screen. If a negative film image is formed from the video signal, the time required to develop it into a positive film image will be added. For these reasons, these methods and apparatus have limited testing capability.

All of the methods and apparatuses that have been described so far involve a human operator's intervention, such as visual checking. This imposes restrictions on the efficiency and precision that may be provided by them. Also, these methods and apparatuses cannot be employed on an automatic-flow line. In this respect, they have serious problems and drawbacks.

SUMMARY OF THE INVENTION

An object of the present invention is to provide a testing method that is specifically designed to examine the contents in a package in a non-destructive manner. More specifically, the method according to the present invention is characterized by the fact that a package, such as cans, bottles and the like, which contains a liquid or other fluid article, is first shaken under a predetermined vibrating condition, the package is then exposed to an irradiation of ultra-soft X-ray beams that are directed against its surface either while the package is still vibrating or immediately after it ceases to vibrate, the strength of X-ray beams that have been transmitted through the contents inside the package are determined by using an X-ray beam detector or meter, and there can be detected any material alteration and/or the magnitude thereof due to any change in the density per unit volume due to the mixing of the gas in the head space and the contents. Through these steps, it is finally possible to determine whether there is any abnormal material property alterations, and to determine the degree or magnitude of those alterations. The X-ray beam detector or meter provides a signal output in response to the strength of the transmitted X-ray beams as detected by it, which represents the particular density due to the gas in the head space being mixed with the contents. This signal output provides the basis for determining the presence or absence of the abnormal material alterations and/or the magnitude or degree thereof. The method and apparatus that implement the above concept have not heretofore been known to the relevant field.

The term "abnormal material alterations" that has been referred to so far and will be referred to hereinafter may include any unacceptable material alterations or defects in the density, viscosity and composition, as well as any unacceptable bacterial alterations in the food, medicine and the like.

One aspect of the present invention is to provide a method that allows the package or like container to be examined in a non-destructive manner, thereby determining whether there are any abnormal material alterations in its fluid content. According to the method, a package, bottle or the like, which contains material in its normal or non-altered original condition, is initially shaken under a predetermined vibration condition, thereby causing its contents and any gaseous substance which may be contained in the package to be mixed together. The package and its contents are shaken further until they reach their natural resonance frequency. Then, while they are vibrating at said natural resonance frequency, the package is exposed to an irradiation of ultra-soft X-ray beams against the surface of the package. The strength of the X-ray beams that have been transmitted through the package and its contents are detected by an X-ray beam detector or meter, which provides a signal output that represents the strength of transmitted X-rays when the material contained in the package is in its normal or non-altered condition. The above output signal constitutes a reference signal. At the time when the similar contents of other packages are to be examined, the steps as described above are repeated under the same conditions, and another signal output is provided by the X-ray beam detector or meter which detects the strength of X-rays that have been transmitted through the package while it is vibrating under the same condition at which the above natural resonance frequency vibration is obtained. This output signal value is then compared to the reference output signal value previously obtained, from which an difference is obtained. This difference will show any abnormal material alterations and/or the magnitude thereof.

Another aspect of the present invention is to provide a method that allows a package or like container to be examined in a non-destructive way, thereby determining whether there are any abnormal material alterations in its fluid content. According to the method, a package, bottle or the like, which contains material in its normal or non-altered original condition, is initially shaken under a predetermined condition, thereby causing its contents and any gaseous substance also contained in the package to be mixed together. Then, either immediately after they begin to be agitated due to shaking, or immediately after vibration is stopped and they cease to be agitated, the package is exposed to an irradiation of ultra-soft X-ray beams against the surface of the package. The strength of the X-rays that has been transmitted through the package and its contents are detected by an X-ray beam detector or meter, which provides a signal output that represents a strength of transmitted X-rays when the material is contained in the package in its normal or non-altered condition. The above output signal constitutes a reference signal. At the time when the similar contents of other packages are to be examined, the steps as described above are repeated under the same conditions, and another signal output is provided by the X-ray beam detector or meter which detects the strength of X-rays that have been transmitted through the package either immediately after they begin to be agitated by shaking or immediately after the vibration is stopped and they cease to be agitated under the same conditions. This output signal value is then compared with the reference output signal value previously obtained, from which any difference between them is obtained. This difference will show any abnormal material alterations and/or the magnitude thereof.

For both the methods described above, the materials in the packages or like containers may include liquids. pastes and the like, and the gaseous substances that may be present in the packages may include air or any inert gas such as nitrogen.

Another aspect of the present invention is to provide an apparatus which comprises a shaking device which causes a package to be shaken so as to agitate its contents, an ultrasoft X-ray beam supply source which directs an irradiation of X-ray beams against the package on the shaking device, an X-ray beam detector which is disposed opposite the X-ray beam supply source and detects the strength of any X-rays that are transmitted through the package and its contents, and a package separating device connected to the output of the X-ray beam detector and which is operated to separate the packages in response to the output from the X-ray beam detector. The X-ray beam detector may include an X-ray beam meter which provides an analog signal to be supplied to any appropriate signal processing circuit, combined with any data logger that determines and records the appropriate data which shows whether there are abnormal material alterations or not.

As will be appreciated from the foregoing description, the method and apparatus according to the present invention provides improvement over the prior art method and apparatus that have technical problems such as those described earlier. It will also be understood that the present invention may be employed in an automatic flow-line manufacturing environment.

As one feature of the present invention, a package that contains a fluid substance is shaken. Shaking the package causes the agitation which will cause the contents and any gas in the head space above it to be mixed together. As the package begins to be agitated, that part of the gas in the head space located nearest to the surface of the contents will first change into fine gas bubbles which enter the contents, followed by remaining parts located farther away from the surface that also change into fine bubbles which enter the contents. Thus, the gas bubbles and contents are mixed together. The package continues to be shaken until the package and its contents reach their natural resonant frequency, when the bubbles have entered into the entire contents and the resulting mixture has become uniform. When the uniform mixture has been obtained, the contents have the smallest density at the middle of the package. If the vibrating energy which is being applied to the package is further increased after the package and its contents have reached the natural resonant frequency, the resonant vibration of the package and its contents will be stopped, and the rate at which the bubbles and contents are mixed together at the middle of the package will be reduced.

It is noted that the strength of the X-ray beams that pass through a medium is decreased the greater then density of the medium. Any change in the strength will be detected by an appropriate X-ray beam detector or meter, and will provide the basis for determining the corresponding substance property alteration that may occur to the contents inside the package with regard to any particular reference data previously obtained. As the ratio of the contents and air bubbles increases, the density is decreased accordingly, which allows a greater portion of X-rays to be transmitted through the contents.

It is known in the vibration dynamics field that the vibration conditions under which two different objects, such as a package and its contents in this case, vibrate at the greatest resonance may depend upon some physical variables such as the quantity, density and viscosity of the contents, and the property of the material in the package, and may be expressed in terms of certain value ranges of those variables. It is also known in this field that the resonance will occur under certain vibrating conditions as long as those variables have a constant value. It should be noted, however, that when two different substances, such as liquid detergent and salt solution, have an identical viscosity and density but may have different properties, the fine air or other gas bubbles that are produced from the head space when the package is vibrating, and enter into the contents may occur in a quite different manner. When the object to be examined is food, the manner in which air bubbles would be produced if any change in the chemical property has been caused by protein decomposition may differ from that in the normal situation, even though there is no change in the viscosity when the protein decomposition occurs. Furthermore, when the vibrating condition under which the package under examination containing any adversely affected substances produces vibrations at the natural resonance frequency and the vibrating condition under which the package under examination containing no adversely affected substances produces vibrations at the natural resonance frequency are close (such as foods that contain a particular bacteria that have grown, and foods that don't), the rates at which the produced air bubbles are mixed with the package contents are different. For these reasons, the method according to the present invention makes it possible for packages containing adversely affected substances to be detected.

When a package that contains a particular fluid material is to be examined, the package is shaken by any mechanical means or manually, with the thickness across its central portion being constant and subjected to an irradiation of ultra-soft X-ray beams, and a chaotic motion is thus caused over the surface of the contents within the package. As the applied vibration energy is increased, the gas in the head space is diffused into the contents. As the package and its contents reach the resonant frequency, the gas in the head space that has been diffused into the contents is changed to fine air bubbles which are uniformly mixed with the contents at the resonant frequency. The package is thus filled with the resultant uniform mixture. Either in this state or immediately after the package ceases to vibrate, an irradiation of ultra-soft X-ray beams is directed against the surface of the package, and the package, including the central portion of the package, in which the uniform mixture of fine air bubbles and contents is formed will have the lowest density at that time, and the largest strength X-rays will be transmitted through that portion at that time. The vibrating condition at which the resonance frequency vibration appears, and the length of time required from the beginning of agitation by a shaking operation until the time when the resonance frequency vibration is reached, or the length of time required from the end of the resonance frequency vibration until the produced air bubbles disappear may vary in response to any change in the property of the contents, if the types or forms and volume of packages and the quantity of contents contained in the packages are identical. It will be understood from the above fact that when a package containing a material whose property is affected by any alteration is shaken under the same vibrating condition as one not affected by any alteration and which has been shaken in order to provide a certain reference strength of the transmitted X-ray beams, the strength of the transmitted X-ray beams will be different for the package with the non-altered contents. This difference between the strengths of the transmitted X-ray beams will help determine whether there are any property alterations or not and/or the magnitude or degree thereof. When the vibrating conditions under which these two packages are shaken to provide the vibration at resonance frequencies, and the lengths of time required from the beginning of the shaking operation until the resonance frequency is reached are very close, respectively, there will be a difference between the rates at which the produced air bubbles disappear. In such a case, any property alteration can still be detected from the difference between the strengths of the transmitted X-ray beams for the two packages.

The packages may be made of a metal foil, a combination of metal foil and any plastic and/or laminated sheet paper, a single-layer or multiple-layer plastic, metal evaporated film, paper, laminated paper and plastic, or a resin-coated cloth. Packing materials that are used to supplement the packages may include carton and kraft paper, as well as the materials listed above.

The packages may be of any type or form, including bottles, containers, bagging boxes, flat bags, self-standing bags, tubes, cartons, composite cans, paper cans, aluminum cans, and the like.

The materials which are contained in the packages may include food, medicine, animal food, reagents, and the like. In particular, food and medicine which might affect human life if they are altered should require the most careful examination. The materials may have any form, such as uniform liquids, non-uniform liquids, pastes, and any other fluid forms.

The ultra-soft X-ray beams refer to X-ray beams in the wavelength range spectrum located near the ultraviolet rays, and this term may be used to distinguish between the normal X-ray beams in the wavelength range located near the $\gamma$-ray beams.

The X-ray beams meter means includes slits through which the beams transmitted through the material in the package are passed, and a fluorescent light emitter which converts the transmitted X-ray beams to the corresponding amount of light. The light is fed to a photomultiplier which converts the input light to a flow of electrons. This flow of electrons is applied to an electron amplifier which provides current output after amplification. The X-ray beams meter means can be any type that can convert X-ray beams into the corresponding analog electrical signal, such as a scintillation counter. The electrical signal is further applied to a signal processing circuit which provides the amplifier and comparator functions to allow the input electrical signal to be amplified and compared with the reference value for the package being tested.

The package may be subject to deformation when it is being shaken and agitated, causing variation in the thickness across the area through which the X-ray beams are to be transmitted. If this occurs, the detector will not detect accurately. In order to avoid this situation, the shaker includes a package retainer specifically designed to conform with the material strength of the package, thereby preventing the package from deforming under the applied shaking force.

The method and apparatus of the present invention that have been described so far make it possible for the contents within all packages to be checked to see whether the contents contain any property alterations or defects, without destroying the packages. Thus, none of the packages will be wasted during examination. In addition to the above, the magnitude or degree of any alterations that may be found can also be determined. The examination involves no visual checking, which allows the total number of examined packages to be counted. The method and apparatus according to the present invention provides advantages when they are applied in the relevant industry, particularly in the food processing and medicine manufacturing industries.

In particular, the apparatus according to the present invention may form part of an automatic production flow line, and may also be coordinated with any other production line. Thus, high working efficiency, high precision requirements and fully automatic producing can be satisfied.

BRIEF DESCRIPTION OF THE DRAWINGS

These and other objects, advantages, and features of the present invention will become apparent from the detailed description of several preferred embodiments with reference to the accompanying drawings, in which.

DETAILED DESCRIPTION OF PREFERRED EMBODIMENTS

An example of the apparatus embodying the present invention will now be described with reference to the drawings.

Figure 1:
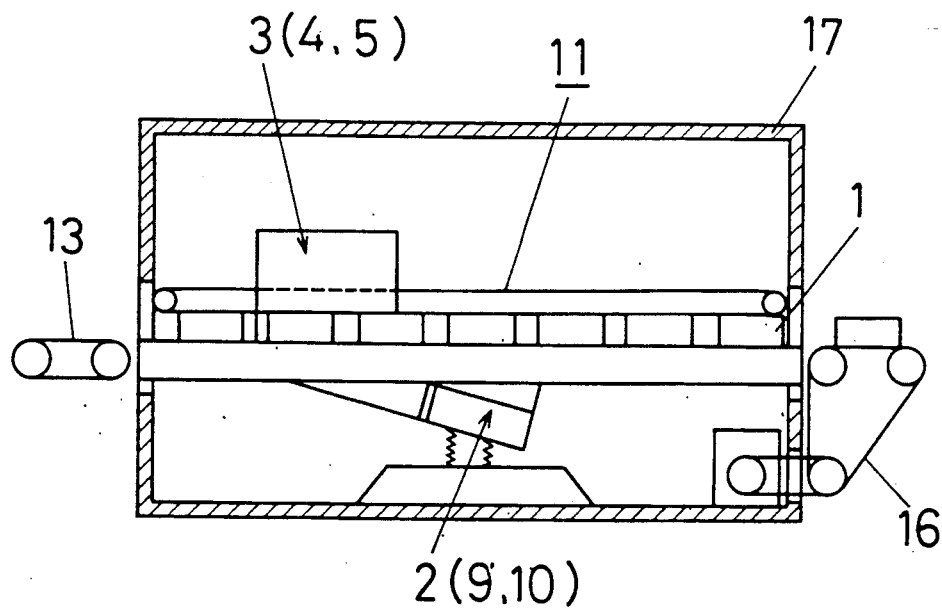
FIG. 1 is a front elevation view illustrating the apparatus embodying the present invention in partly cross-section.
Figure 2:
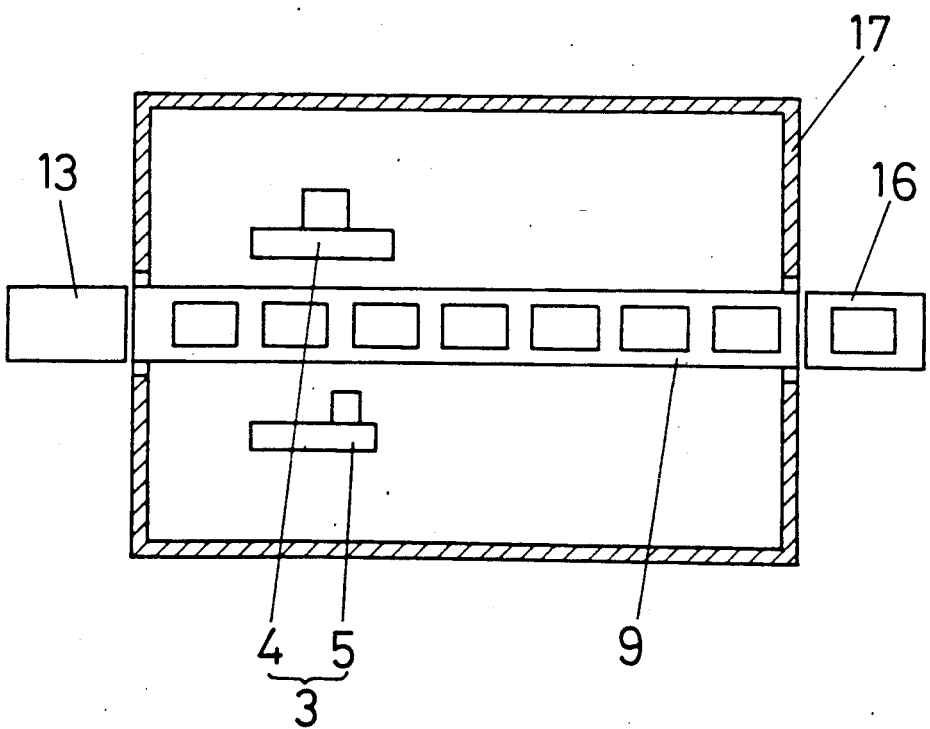
FIG. 2 is a plan view illustrating the apparatus as shown in FIG. 1 in partly cross-section.

Referring to FIGS. 1 and 2, the apparatus according to the present invention includes shaker means 2 for causing a package 1 to vibrate and main detector means 3 which is disposed separately from and in parallel with the shaker means 2. It should be understood that the main detector means 3 is physically and mechanically separate from the shaker means, rather than integrally with the latter, because the vibrations produced by the shaker means 2 would otherwise be imparted to the main detector means 3, which would cause the ultra-soft X-ray beams emitter 4 to make the X-ray beams out of focus. This would cause the X-ray beam detector or sensor 5 to respond to the out-of-focus X-ray beams that have been transmitted through the package and provide corresponding variant output signals. The arrangement shown can meet the requirements for isolating the main detector means 3 from the vibrations caused by the shaker means 2.

Figure 3:
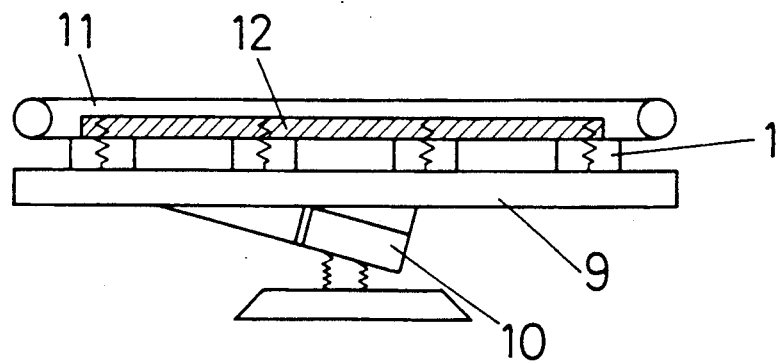
FIG. 3 is a schematic diagram of an example of a shaker which may be included in the preferred embodiment, in which some essential parts of the shaker are shown.

The shaker means 2 includes a conveyor 9, a vibration generator 10, and other elements or parts operatively associated with the conveyor and vibration generation, as shown by FIG. 3. The conveyor 9 carries package 1 thereon toward the downstream side thereof. The vibration generator 10 produces vibrations which are transmitted to the package 1 travelling with the conveyor 9. This vibration generator 10 may have the form of an electric motor vibrator, an electromagnetic vibrator that provides an attractive force, a vibration motor, a mechanical vibrator, or any other known type of vibration generating device. A package retainer 11 is provided for holding the package 1 travelling on the conveyor 9 so that the package will maintain a constant thickness, which would be affected by any deformation that would otherwise occur. This package retainer 11 is disposed above (and on the opposite sides of) the conveyor 9 and parallel with it. Preferably, means may be included to permit the package retainer 11 to be brought closer to or moved further away from the conveyor 9 and to permit it to follow the conveyor 9 that is travelling, when it engages the package 1. Preferably means may be provided for allowing the package retainer 11 to synchronize with the shaker means, thereby providing a smooth shaking motion.

Figure 4:
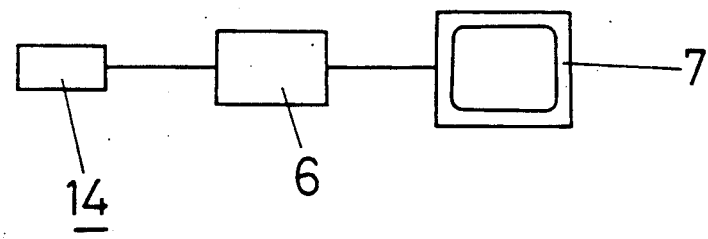
FIG. 4 is a block diagram showing a detector which may be included in the preferred embodiment.

The main detector means 3 includes an ultra-soft X-ray beam emitter 4 on one side of the conveyor and an X-ray beam detector 5 at the opposite side. The ultra-soft X-ray beam emitter 4, which can be a Softex Co., Ltd. Model XV-100A with a maximum power output of 100 KVP at 5 mA, sold by Softex Co., Ltd. of Japan, directs its ultra-soft X-ray beams against the package 1. The X-ray beam detector 5, which can be an X-ray beam meter sold by Softex Co., Ltd. of Japan as model R-1005, includes an X-ray beam sensor 14, a signal processing circuit 6, a data logger 7, as shown by FIG. 4. The X-ray beam sensor 14 responds to any X-ray beams that have been transmitted through the package 1, and converts those X-ray beams to a fluorescent light. This light is fed to a photomultiplier which provides an electron flow, which is applied to a preamplifier that provides current output after amplification. The output signal of the X-ray beam sensor 14 is a unique signal that corresponds to each individual package 1 and which is applied to the signal processing circuit 6 which determines from the unique signal whether the package contains any abnormal alterations and/or the magnitude or degree of such alterations. This information from the signal processing circuit 6 is recorded in the data logger 7 from which it may be displayed.

Preferably, the apparatus according to the present invention may further include means for separating those packages that have been identified as defective from those that have been identified as non-defective. This separator means 8 may be provided at the end of the main detector means 3. The example of the separator means 8 is shown in FIG. 5.

Figure 5:
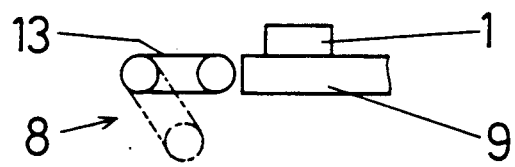
FIG. 5 is a front elevation view showing part of a separator in its specific embodiment.

As seen from FIG. 5, a second conveyor 13 may be provided at the end of the main detector means 3, and may have its one end pivotally supported so that its other (free) end can swing up and down. The second conveyor 13 is operated when a package that has been identified as defective is moving onto the second conveyor 13, and swings downwardly to allow the package to be separated from the non-defective package.

Figure 6:
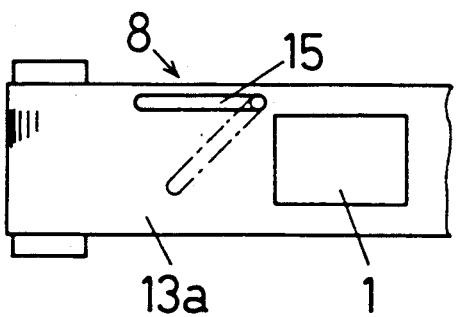
FIG. 6 is a plan view showing the same part of the separator as shown in FIG. 5.

An alternative form of the separator means 8 is shown in FIG. 6. As seen from FIG. 6, a guide rail 15 may be provided at the end of the main detector means 3 or on the second conveyor 13 contiguous with the main detector means 3, and can be controlled so that it can turn in one or the other direction, depending upon whether a package has been identified as defective or not. Thus, the guide rail 15 can guide the packages in different directions, according to the packages identified as defective or not. In FIGS. 1 and 2, reference numeral 16 denotes a package delivery conveyor, and 17 denotes an X-ray beam shield.

As described above, each individual package, bottle, can, or the like that contains an object to be examined, such as food, is checked to see whether the object contains any alteration, and the separator means 8 causes those individual packages identified as defective to be separated from those identified as non-defective.

The ultra-soft X-ray beam supply source and the X-ray beam detector may be of any known type, and each individual package may be started or stopped at any time.

EXAMPLE 1

In this example, a package is formed by a polyethylene bottle having a 55 mm diameter, 165 mm height, and 0.7 mm thickness, and a processed milk hermetically filled into the bottle. Three kinds of processed milk were used, and each of them was contained in a respective bottle. One bottle contained milk that had just been processed and was subjected to no further processing (which will hereinafter be referred to as "unaltered milk"). Another bottle contained processed milk which contained an arbitrary kind of strain of bacteria which had been added thereto and which had been left to grow for four or five days at room temperature (which will hereinafter be referred to as "pre-stage altered milk"). The third bottle contained an arbitrary kind of strain of bacteria which had been added thereto and had been left to grow for two weeks at room temperature (which will hereinafter be referred to as "post-stage altered milk"). The above-identified Model SV-100A, which provides a maximum power output at 100 KVP at 5 mA, was used in this example.

The testing proceeded as follows:

Each bottle which contained one of the respective kinds of processed milk was first shaken by a shaker. This shaking continued until the bottle containing the unaltered milk and its contents vibrated at the natural resonance frequency. At this point, all three bottle were exposed to an irradiation of ultra-soft X-ray beams supplied at a output power of 55 KVP, at 3 mA. The amount of X-ray beams transmitted through the middle portion of each respective bottle was detected by using the above-identified X-ray beam meter Model R-1005. The output of the transmitted X-ray beams as detected by the detector was substantially equal to 270 mV for the unaltered milk, whereas it was as low as 160 mV at the maximum for both the pre-stage and post-stage altered milk under the same vibration condition. It should be noted that the unaltered milk had a viscosity of 1.84 CP at 20° C., and the altered milk had a viscosity of 1.50 to 247.50 CP at 20° C. It has been found that the method according to the present invention may be used to distinguish the altered milk from the unaltered milk although some altered milk has the same viscosity as that of unaltered milk. Tests under the same conditions as described above were carried out in which the bottles were covered with an aluminum-laminated film having respective different thicknesses of 7 µm, 15 µm and 20 µm and also using a double flute carton, and in which double flute cartons with the respective aluminum-laminated films were used. The same results were obtained for those bottles.

EXAMPLE 2

In this example, the examination was conducted in the same manner as in the preceding example, for the bottles which contained the unaltered processed milk and for the bottles which contained the altered processed milk to which an arbitrary strain was added and which had been stored for six weeks in a refrigerator at 10° C.

The results obtained during the examination showed that the X-ray beam detector provided an output of 250 mV on average for all of the unaltered milk bottles whereas it provided an output of below 170 mV for most of the altered milk bottles. Some of the altered milk bottles examined had a viscosity of 1.75 CP, for which the detector provided an output of 240 mV on average, and the length of time required from the beginning of vibration until natural resonance frequency was reached was close to that for the unaltered milk bottles. 0.8 seconds after vibration was stopped, the output of the detector was equal to 0 mV for the unaltered milk bottles (which corresponds to the value of the output detected when the bottles were not vibrating), whereas the output of the detector was as high as 200 mV on average for the altered milk bottles. Thus, it has been found that when the altered milk bottles cannot be identified at natural resonance frequency, it is possible to identify them by directing the ultra-soft X-ry beams against them immediately after they cease to vibrate.

EXAMPLE 3

Pater cartons having a bottom of 95 mm × 63 mm, a height of 175 mm and a volume of 1,000 ml were provided, and unaltered, pre-stage and post-stage milk, all of which were previously processed and prepared as described in Example 1, were hermetically sealed in respective ones of the cartons. The examination was also conducted in the same manner as described in Example 1, by using the above-described ultrasoft X-ray beam emitter Model SV100A, and the X-ray beam meter Model R-1005. Each of the paper cartons used for the examination had a five-layer structure consisting of an outer 15 µm-thick polyethylene film layer, 260 µm-thick diplex paper layer, 25 µm-thick polyethylene film layer and 7 µm-thick aluminum foil layer forming the intermediate layers, and an inner 45 µm-thick polyehtylene layer.

The results obtained show that the detector provided an output of 300 mV for the unaltered milk cartons, whereas it provided a maximum output of as low as 180 mV for the prestage and post-stage altered milk cartons. Those cartons could thus be identified. The altered milk had a viscosity of 1.68 CP at 20° C., while the unaltered milk had a viscosity of between 1.45 CP and 55.50 CP. Some of the altered milk had a viscosity almost equal to that of the respective unaltered milk, and they could be identified. Another testing occurred for those cartons which were supplemented by a double-flute carton, and the same results were obtained.

EXAMPLE 4

The testing was conducted on food-containing aluminum cans, using as a reference cans containing food for weaning children having a viscosity of 2.5 CP at 20° C., and testing for aluminum cans containing similar food the density of which might be altered (such as to be watery) at the beginning of the manufacturing process. Aluminum cans containing both types of food were examined in a consecutive manner by using the above-described apparatus of the present invention. The examination was carried out by exposing them to irradiation by ultra-soft X-ray beams and detecting any alterations under the same conditions as described in Example 1. The shaking conditions were chosen such that the aluminum cans containing the reference foods would vibrate at the natural resonance frequency. Through the examining steps, the aluminum cans which contained the altered or watered foods having a density less than 1.8 CP at 20° C. could be identified.

EXAMPLE 5

The testing was conducted for packing containers having a four-layer structure consisting of an outer 12 μm-thick polyester film, an intermediate 9 μm-thick aluminum foil and 15 μm-thick two-axial rolled nylon film, and an inner 70 μm-thick polyethylene film. The packing containers contained 200 ml of soup. Some of the packing containers contained soup that was just processed (unaltered soup), others contained soup was was processed and then left for four or five days at room temperature (pre-stage altered soup), and the remainder contained soup that was processed and then left for two weeks at room temperature (post-stage altered soup). The examination was conducted by using the same apparatus as for Example 1 and in the same manner, except that the power output was 40 KVP at 3 mA. The results show that the output from the detector for the pre-stage and post-stage altered soup containers was low, as compared with the output for the unaltered soup containers. The smallest output difference was equal to 50 mV, which was sufficient to distinguish the unaltered soup containers from the others.

EXAMPLE 6

The testing was conducted in the same manner as in Example 1 for 2 ml plastic cups respectively containing 1 ml of three types of cream, except that the power output of the ultra-soft X-ray beams was 10 KVP at 2 mA. The results show that the output from the detector for the pre-stage and post-stage altered cream cups was low, as compared with the output for the unaltered cream cups. The smallest output difference was equal to 20 mV, which was sufficient to distinguish the unaltered cream cups from the others.

EXAMPLE 7

The testing was conducted in the same manner as in Example 1 on polyester bottles having a bottom of 70 mm×40 mm, a height of 150 mm and a thickness of 0.5 mm and which contained 250 ml of India ink hermetically sealed therein, and on similar bottles that initially contained 250 ml of India ink not hermetically sealed therein and which had been left for 20 days in a 30° C. temperature-controlled room and then kept in hermetic containers. The former bottles contained unaltered ink as a reference, and the latter bottles contained altered ink. The shaking condition was chosen such that the unaltered ink bottles and their contents would vibrate at the natural resonance frequency. The detector power output was 50 KVP at 3 mA.

, For the unaltered ink bottles, the natural resonance frequency was reached 2.25 seconds after they began to vibrate due to the applied shaking motion and the output of the X-ray beam meter increased to about 50 mV, whereas for the altered ink bottles, no resonance effec was present 2.25 seconds later, and the output of th X-ray beam meter remained unchanged, as compare( with that prior to the shaking motion. The resonanc vibration appeared 11.20 seconds later.

A detector like that in Example 2 was used with th bottles in this example. The testing occurred under th above shaking conditions, and the output provided b; the detector 5 seconds after the shaking motion begai helped to identify the unaltered and altered ink bottle:

EXAMPLE 8

Vinyl chloride containers which held 20 cc of liqui( retoucher were examined in the same manner as in Ex ample 6, to verify the quality of their contents. Th( shaking conditions were chosen such that the unalterec contents and their containers would vibrate at the natu ral resonance frequency and the altered (hardened contents and their containers underwent no resonanc( vibration when the containers were shaken under th( chosen shaking conditions. The output of the detecto remained unchanged, as compared with that prior to th( shaking motion. Thus, the containers with the defectiv( retoucher could be identified.

Although the present invention has been described ii detail with reference to the various preferred embodi ments thereof, it should be understood that variou: changes and modifications may be made without de parting from the spirit and scope of the invention.

What is claimed is:

1. A non-destructive testing method for enablinε examination of a package constituted by a container anc fluid content to be examined to determine whethe: there has been any unacceptable alteration of the prop erties of the fluid content, the method comprising th( steps of:

shaking the package of the container containing th( fluid content in its unaltered state under a predeter mined vibrating condition for causing the fluic content and any gaseous substance also containec in said container to mix together;

causing said package to vibrate under said vibratinε condition until it vibrates at the natural resonanc( frequency of the package;

exposing said package including the fluid conten therein to an irradiation of ultra-soft X-rays whilε said package is vibrating at the resonance fre quency;

detecting the strength of said ultra-soft X-rays that have been transmitted through said package as ε reference value;

repeating the said shaking, vibrating and exposinε steps for other packages each having a containei containing the same fluid content but the amount oi alteration of the properties of which is unknown and obtaining a specific value of the transmittec X-ray strength for each of said other packages;

comparing each such specific value with said refer ence value and determining any difference betweer said each specific value and said reference value and determining from said differences whether there i: any unacceptable alteration of the properties of th( fluid content in each of the said other packages.

2. A non-destructive testing method for enablinε examination of a package constituted by a container anc fluid content to be examined to determine whethei there has been any unacceptable alteration of the properties of the fluid content, the method comprising the steps of:

shaking the package of the container containing the fluid content in its unaltered state under a predetermined vibrating condition for causing the fluid content and any gaseous substance also contained in said container to mix together;

causing said package to vibrate under said vibrating condition until it vibrates at the natural resonance frequency of the package;

stopping said vibrating and immediately exposing said package including the fluid content therein to an irradiation of ultra-soft X-rays;

detecting the strength of said ultra-soft X-rays that have been transmitted through said package as a reference value;

repeating the said shaking, vibrating, stopping and exposing steps for other packages each having a container containing the same fluid content but the amount of alteration of the properties of which is unknown, and obtaining a specific value of the transmitted X-ray strength for each of said other packages;

comparing each such specific value with said reference value and determining any difference between said each specific value and said reference value; and determining from said differences whether there is any unacceptable alteration of the properties of the fluid content in each of the said other packages.

3. A method as claimed in claim 1 or claim 2 in which said fluid content is liquid or paste, and said gaseous substance is a gaseous substance taken from the group consisting of air and inert gas.

4. An apparatus for enabling non-destructive testing of a package constituted by a container and fluid content to be examined to determine whether there has been any unacceptable alteration of the properties of the fluid content, said apparatus comprising:

means for supporting a package constituted by a container and fluid content to be examined so that i can be vibrated;

means for vibrating said supporting means and package supported thereon at a vibration frequency for vibrating the package at the natural resonant frequency of the package;

means for retaining said package in said supporting means and mounted for vibrating at the frequency of vibration of said supporting means;

means for directing an irradiation of ultra-soft X-ray through said package on said supporting means;

an X-ray strength detecting means on the opposite side of said package from said X-ray irradiation means for detecting the strength of X-rays which pass through said package and for comparing the detected X-ray strength with a reference X-ray strength for a package the properties of the fluid contents of which are unaltered and producing an output signal when a package the fluid contents of which have been unacceptably altered is detected and package separator means for receiving packages from said supporting means and connected to said detecting means and operable in response to said output signal for separating packages identified as having fluid contents the properties of which have ben unacceptably altered.

5. An apparatus as claimed in claim 4 in which said detector means includes X-ray beam meter means for sensing the X-rays passed through the package being tested and producing an output, signal processing means for providing a signal representative of the strength of the X-rays passed through a package being tested form the output of said X-ray beam meter, and data logger means connected to said signal processing means for comparing the output of said signal processing means and comparing it with a reference value and determining and recording whether there is a defect in the package being tested.

* * * * *